(12) United States Patent
Lemaitre

(10) Patent No.: US 8,672,948 B2
(45) Date of Patent: Mar. 18, 2014

(54) VERTEBRAL SPACER SIZE INDICATOR

(75) Inventor: Philippe Lemaitre, Crozet (FR)

(73) Assignee: Warsaw Orthopedic, Inc., Warsaw, IN (US)

( * ) Notice: Subject to any disclaimer, the term of this patent is extended or adjusted under 35 U.S.C. 154(b) by 309 days.

(21) Appl. No.: 13/283,254

(22) Filed: Oct. 27, 2011

(65) Prior Publication Data

US 2013/0110121 A1   May 2, 2013

(51) Int. Cl.
*A61B 17/56* (2006.01)

(52) U.S. Cl.
USPC .............................. 606/102; 33/512; 33/836

(58) Field of Classification Search
USPC ........ 606/102, 86 R, 90, 53, 105, 87; 33/512, 33/511, 501.45, 542, 836, 152, 551, 759, 33/810; 206/305–306
See application file for complete search history.

(56) References Cited

U.S. PATENT DOCUMENTS

| | | | | |
|---|---|---|---|---|
| 3,706,307 A | * | 12/1972 | Hasson | 600/591 |
| 4,362,167 A | * | 12/1982 | Nicolai et al. | 600/591 |
| 6,427,351 B1 | * | 8/2002 | Matthews et al. | 33/512 |
| 2003/0047009 A1 | * | 3/2003 | Webb | 73/862.541 |
| 2005/0203541 A1 | * | 9/2005 | Steffensmeier et al. | 606/102 |
| 2008/0005916 A1 | | 1/2008 | Francis et al. | |
| 2010/0010494 A1 | | 1/2010 | Quirno | |

* cited by examiner

*Primary Examiner* — Todd Manahan
*Assistant Examiner* — Marcela I Shirsat

(57) ABSTRACT

A disposable measuring device for use in measuring the width, height and depth of an intradiscal space is provided, the device including an elongated body having an upper surface, a lower surface, a proximal end and a distal end. The elongated body also has a first pair of members configured for receiving a first cursor slidably arranged for measuring a width dimension, a second pair of members configured for receiving a second cursor slidably arranged for measuring a height dimension; and a detachable stop operatively connected to the first pair of members and the second pair of members, the detachable stop insertable into at least one opening located at the proximal end of the elongated body, the detachable stop configured for measuring a depth dimension.

19 Claims, 4 Drawing Sheets

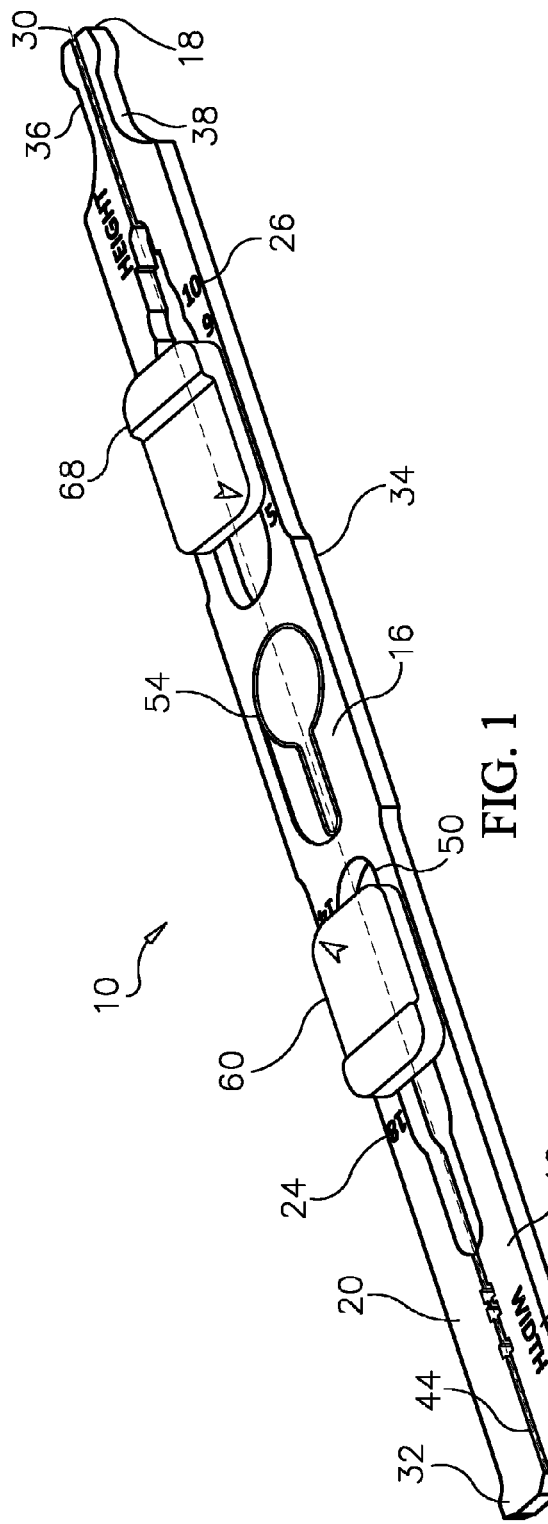
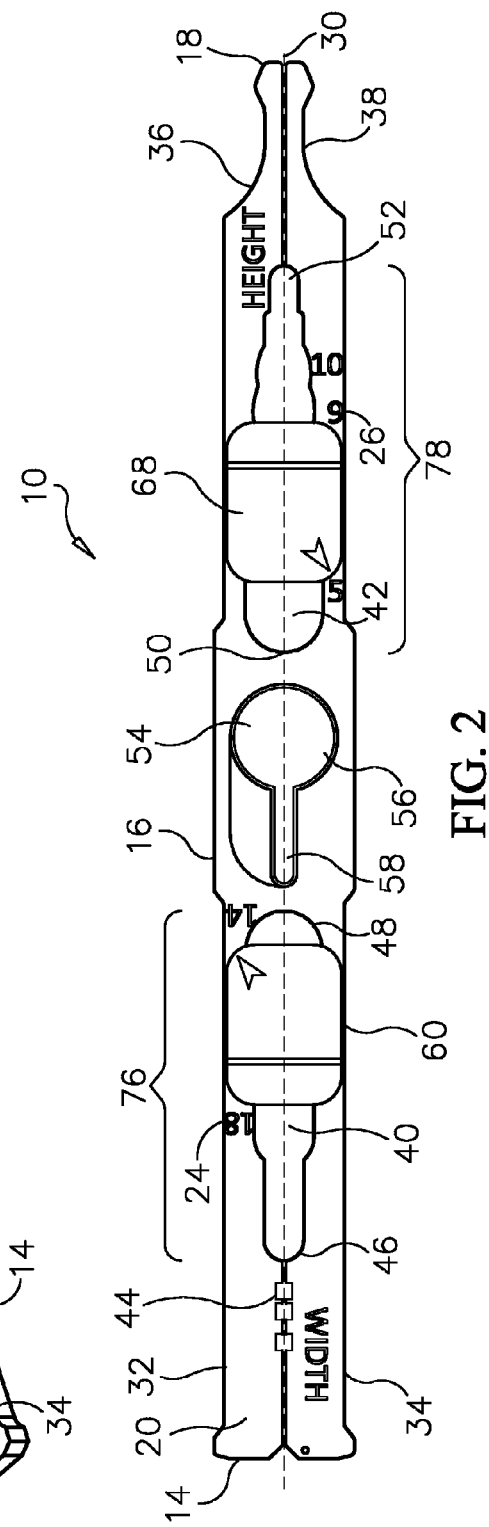

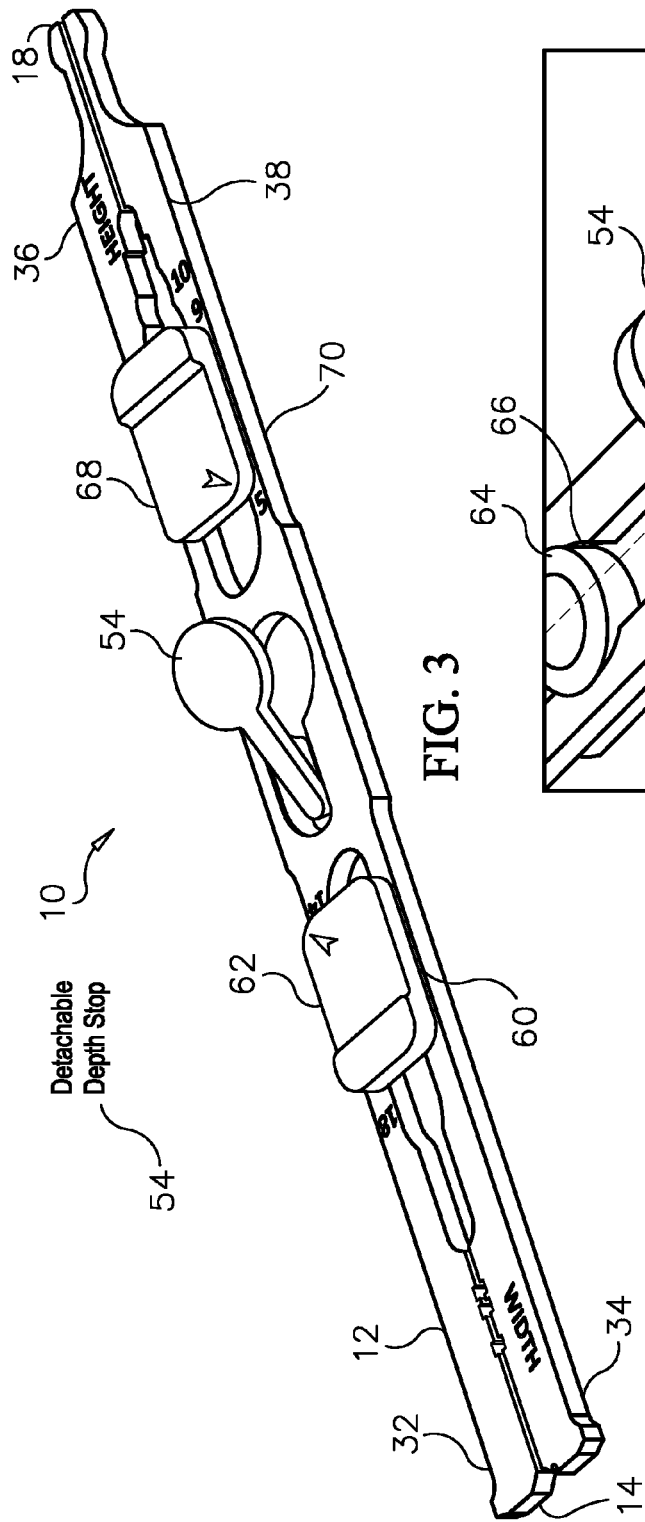
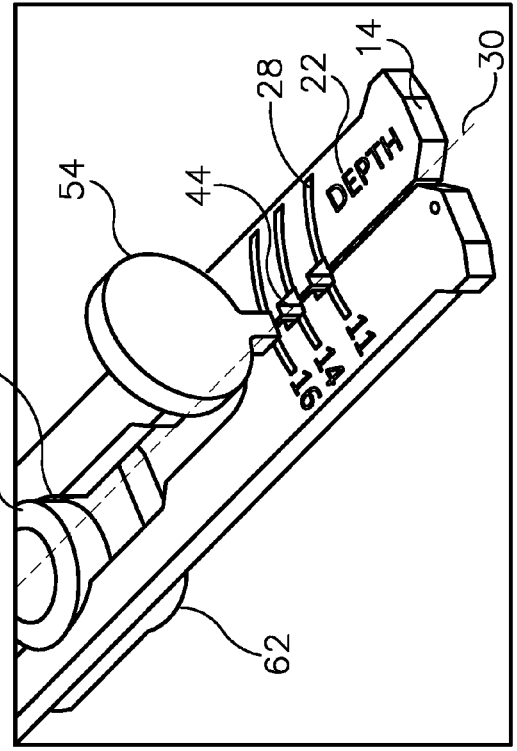
FIG. 3
FIG. 3A

VERTEBRAL SPACER SIZE INDICATOR

TECHNICAL FIELD

The present disclosure generally relates to surgical measuring devices, and more particularly to an intradiscal measuring device for selecting an optimal size intervertebral implant.

BACKGROUND

Chronic lower back pain caused by degenerative disc disease is one of the leading causes of disability in adults. Intervertebral disc degeneration can occur as part of the normal aging process in which the nucleus of the disc dehydrates, reducing the shock absorbing capability of the disc. Patients who fail to obtain adequate pain relief from non-surgical treatment (e.g., rest, pain medication, physical therapy, exercise, epidural steroid injections, chiropractic manipulation, ultrasound, massage, orthotics, etc.) may require spinal surgery to alleviate discogenic pain and disability.

One method of treating degenerative disc disease is spinal fusion or arthrodesis surgery in which the affected vertebrae are fused together using a bone graft. During spinal fusion, a perforated titanium cage may be surgically implanted within the space between two adjacent vertebrae after the pain-generating intervertebral disc is removed. The implanted spinal fusion cage must be appropriately sized to restore the normal disc height at the affected vertebral segment. The fusion cage is packed with bone graft, which grows through the perforated walls of the cage and eventually forms a solid bond or fusion with the adjacent vertebrae to prevent motion in the affected vertebral segment and to reduce chronic discogenic pain.

Currently, surgeons must rely on their experience and "feel" when using intervertebral spreaders or distractors to spread the affected intervertebral segment during total disc replacement (TDR) or fusion surgery. Both the artificial disc and fusion cage must fit in a "snug" intervertebral space that has appropriate ligament tension. Too much distraction by the surgeon performing a TDR procedure will result in the placement of an implant that is too large for the intervertebral segment, reducing the ideal range of motion that the implant can provide. In contrast, insufficient ligament tension will not produce enough force on the endplates of the arthroplasty, resulting in loosening and potential migration of the implant from its optimal position. Similarly, since fusion cages or devices should be placed in a stretched intervertebral segment for better fusion, insufficient ligament tension may result in an unsatisfactory fusion and/or undesired range of motion of the affected vertebral segment.

In addition, anterior and posterior pre- and post-distraction disc heights are important parameters for a surgeon to consider when placing an intervertebral disc arthroplasty. It is believed that there is an optimal window of anterior and posterior disc height that allows the optimal range of motion by the arthroplasty. At present, surgeons must either "eyeball" anterior and posterior disc heights before and after distraction on a fluoroscope, and/or use trial devices to measure the size of the intervertebral space by forcing different test devices into the space between adjacent vertebras until the correct sized one is placed. Such trial or test devices are frequently manufactured from expensive metals, such as titanium, and thus are not easily disposable and, as a result, their use is costly.

Yet another parameter for a surgeon to consider when placing an intervertebral disc arthroplasty is the depth of the patient's vertebral endplate. New arthroplasties should cover the entire vertebral endplate outer-rim because this is where the strongest bone lies. However, neither conventional distractors/spreaders nor fluoroscopes provide a surgeon with the precise depth of the patient's vertebral endplate to select the correct size arthroplasty or fusion device that will cover the maximum amount of outer rim.

It is, therefore, desirable to reduce post-operative complications of spinal fusion and TDR arising from improper selection, sizing and placement of the artificial disc or fusion cage by utilizing a measuring device and method capable of sizing the spinal implant according to the natural dimensions and geometry of the intervertebral disc that is to be replaced or augmented. There is, thus, a need for devices and methods for measuring parameters of an intervertebral disc space in all three dimensions. More particularly, there is a need for devices and methods that enable measurements of the intervertebral disc space to be made in a minimally-invasive manner, are easily disposable and are inexpensive.

SUMMARY

Accordingly, a measuring device is provided for use as a cervical intervertebral spacer size indicator to measure the width, height and depth of a cervical implant or intradiscal space. The all in one size indicator is disposable and can be used in a minimally invasive manner.

In some embodiments, in accordance with the principles of the present disclosure, the measuring device includes an elongated body having an upper surface, a lower surface, a proximal end and a distal end. The elongated body further includes a first pair of members configured for receiving a first cursor slidably arranged for measuring a width dimension, a second pair of members configured for receiving a second cursor slidably arranged for measuring a height dimension, and a detachable stop positioned in a central portion of the elongated body and operatively connected to the first pair of members and the second pair of members, the detachable stop insertable into at least one opening located at the proximal end of the elongated body and configured for measuring a depth dimension.

In some embodiments, the measuring device is insertable in an intradiscal space and contains markings on its upper surface for measuring width and height dimensions and on its lower surface for measuring a depth dimension. The lower surface of the measuring device and/or the detachable stop can be provided with a marker (e.g., X-ray marker) for detection of the depth dimension via diagnostic methods, such as example, C-arm fluoroscopy.

In some embodiments, the first pair of members of the elongated body of the measuring device defines a first elongated slot configured for receiving a first cursor slidable in the first elongated slot and configured for urging apart the first pair of members until a width dimension can be measured.

Similarly, in another embodiment, the second pair of members of the elongated body of the measuring device defines a second elongated slot configured for receiving a second cursor slidable in the second elongated slot and configured for urging apart the second pair of members until a height dimension can be measured.

In yet another embodiment, the detachable stop from the central portion of the elongated body is removed and inserted into at least one opening located at the proximal end of the elongated body and positioned for measuring a depth dimension.

There is also provided a measuring device fabricated from a medical grade polymer. As a result, the measuring device can be delivered in sterile package and is easily disposable.

In another particular embodiment the measuring device includes an elongated body extending along a central longitudinal axis, the elongated body having an upper surface, a lower surface, a proximal end and a distal end, the proximal end and the distal end operatively connected by a central portion containing a detachable stop. The elongated body of the measuring device further includes a first pair of members extending from the central portion along the central longitudinal axis towards the proximal end of the elongated body, the first pair of members adjacent each other and defining a first elongated slot configured to receive a first cursor slidable to measure a width dimension. The first pair of members also defines at least one opening at the proximal end of the elongated body, the at least one opening configured for receiving the detachable stop insertable into the at least one opening to measure a depth dimension. The elongated body of the measuring device also includes a second pair of members extending from the central portion along the central longitudinal axis towards the distal end of the elongated body, the second pair of members adjacent each other and defining a second elongated slot configured to receive a second cursor slidable to measure a height dimension.

In another aspect, a method of measuring the width, height and depth of an intradiscal space or cervical implant is provided, the method including the following steps: providing a measuring device in accordance with the principles of this disclosure; inserting the first pair of arms into an intradiscal space such that the longitudinal axis of the elongated body is in the same plane as the intradiscal space and slidably adjusting the first cursor to urge the first pair of members apart until the width of the intradiscal space is reached and then reading the width dimension. The method also provides for inserting the second pair of arms into the intradiscal space such that the longitudinal axis of the elongated body is perpendicular to the plane of the intradiscal space and slidably adjusting the second cursor to urge the second pair of members apart until the height of the intradiscal space is reached and then reading the height dimension. The method provided in accordance with this disclosure also provides for inserting the detachable stop in the at least one opening at the proximal end on the lower surface of the elongated body such that the detachable stop is flush with a selected vertebra and a depth dimension of the intradiscal space is reached and then reading the depth dimension.

The method described in this disclosure also provides for marking the detachable stop or the proximal end of the elongated body of the measuring device with a marker, (e.g., X-Ray marker) and then assessing the intradiscal depth by using a visualization technique (e.g., C-arm fluoroscopy).

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

The present disclosure will become more readily apparent from the specific description accompanied by the following drawings, in which:

FIG. 1 is a perspective view of one particular embodiment of the measuring device in accordance with the principles of the present disclosure;

FIG. 2 is a side plan view of the measuring device shown in FIG. 1;

FIG. 3 is a perspective view of an embodiment of the measuring device shown in FIG. 1;

FIG. 3A is a perspective exploded detail view of a portion of the lower surface of the measuring device shown in FIG. 3;

Figure 2A:
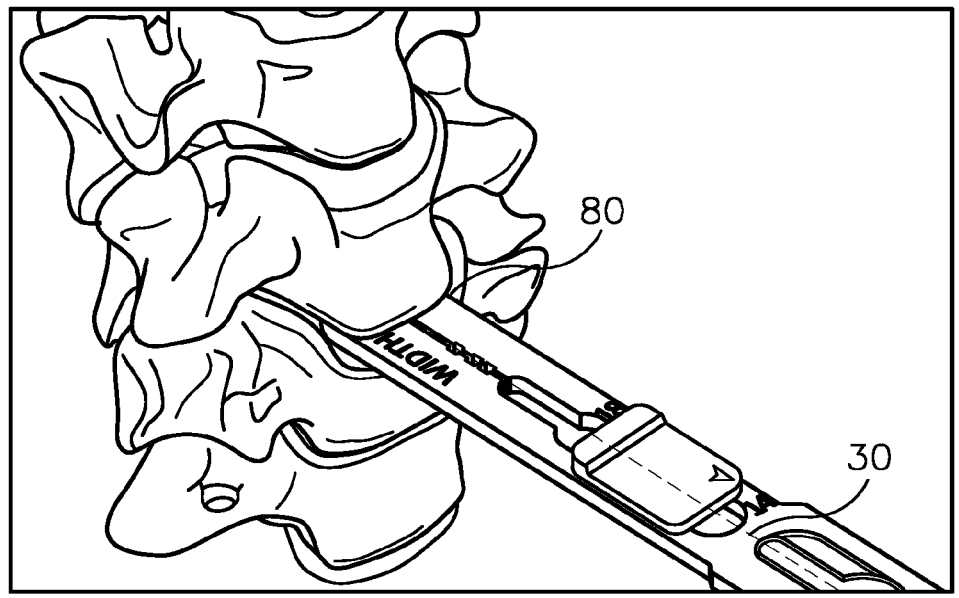
FIG. 2A is a perspective view of a spine section illustrating the measuring device shown in FIG. 1 in operation to evaluate the width of an intradiscal space.

Like reference numerals indicate similar parts throughout the figures. It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

The following description is intended to convey a thorough understanding of the various embodiments by providing a number of specific embodiments and details involving devices for measuring the parameters of an intervertebral disc and/or intradiscal space. It is understood, however, that the embodiments are not limited to these specific embodiments and details, which are exemplary only. It is further understood that one possessing ordinary skill in the art, in light of known systems and methods, would appreciate the use of the embodiments for their intended purposes and benefits in any number of alternative embodiments.

The intervertebral disc or intradiscal space, in some embodiments, can refer to any volume between two adjacent vertebrae. The intradiscal space may be the volume inside of the annulus fibrosus of the intervertebral disc. Alternatively, the intradiscal space also may include the annulus fibrosus itself. The intervertebral disc space may comprise all, or only a portion, of the volume between two adjacent vertebrae.

The present application may be understood more readily by reference to the following detailed description taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

The following discussion includes a description of a disposable measuring device and related methods of employing the measuring device in accordance with the principles of the present disclosure. Alternate embodiments are also disclosed. Reference will now be made in detail to the exemplary embodiments of the present disclosure, which is illustrated in the accompanying figures.

In some embodiments, an all in one vertebral spacer size indicator is provided that is configured to allow assessment of the proper size of implant in the three dimensions, e.g., width, height and depth. In some embodiments, the specific ends at each side of the indicator are configure to act as a template for implant width and height. In some embodiments, two cursors, using the elastic properties of the material, allow adjusting of width and the height of the indicator to cover the full range of implant sizes. In some embodiments, on the central part of the instrument, there is a detachable depth stop, which can be removed and inserted in various sized and shaped holes (e.g., square) designed for that purpose at one of the ends of the size indicator. In some embodiments, this same end is provided with markers allowing the assessment of the intradiscal depth using various diagnostic procedures, such as for example, C-Arm fluoroscopy.

Turning now to FIGS. 1-3C, there are illustrated components of a disposable measuring in accordance with the principles of the present disclosure.

FIG. 1 illustrates a measuring device 10 which includes an elongated body 12 having a proximal end 14, a central portion 16 and a distal end 18, all extending along a longitudinal axis 30 and wherein central portion 16 is operatively connected to and coextensive with proximal end 14 and distal end 18. Elongated body 12 also has an upper surface 20 and a lower surface 22.

A first pair of members 32 and 34 extend from central portion 16 along the central longitudinal axis 30 to proximal end 14 of body 12 and define a first elongated slot 40 configured to receive a first cursor 60.

In an embodiment, it is contemplated that first pair of members 32 and 34 are adjacent mirror images of one another and have a prong or tine shape. Each first member 32 and 34 has a length of from about 40 mm to about 60 mm, a width of from about 12 mm to about 14 mm and a thickness of from about 1 mm to about 3 mm, which thickness is preferably the same as that of elongated body 12.

First elongated slot 40 has a proximal end 46 and a distal end 48 and defines an opening 76 having a length of from about 30 mm to about 35 mm and a width varying from about 4 mm at proximal end 46 to about 8 mm at distal end 48.

In an embodiment, first cursor 60 includes a rectangular surface element 62 attached to a round surface element 64 (shown in FIG. 3A) through a channel portion 66 (shown in FIG. 3A). As shown in FIGS. 1 and 2, upper surface 20 of body 12 contains markings 24 positioned along elongated slot 40 and bearing width units. Upper surface 20 is also marked with the word "width" at a location next to proximal end 14 of body 12. First cursor 60 is configured to slide along width markings 24 of first elongated slot 40. In an embodiment, the rectangular surface element 62 of first cursor 60 is from about 14 mm to about 18 mm in length and from about 10 mm to about 14 mm in width. Round surface element 64 is configured to abut against the lower surface of the elongated member and is slidable along first elongated slot 40. Round surface element 64 of first cursor 60 has a circumference of from about 8 mm to about 10 mm. Channel portion 66 can be from about 6 mm to about 8 mm in width and from about 1 mm to 3 mm in height.

In use, as illustrated in FIG. 2A, it is envisioned that measuring device 10 is inserted into intradiscal space 80 at the proximal end 14 such that the longitudinal axis 30 is in the same plane as intradiscal space 80. The first cursor 60 can then slide along first elongated slot 40 urging first pair of members 32 and 34 apart until a correct width dimension as indicated by markings 24 is reached and the width of the intradiscal space can be read.

With reference to FIG. 1, a second pair of members 36 and 38 extend from central portion 16 along the central longitudinal axis 30 to distal end 18 of body 12 and define a second elongated slot 42 configured to receive a second cursor 68.

In an embodiment, it is contemplated that second pair of members 36 and 38 are adjacent mirror images of one another and have a prong or tine shape. Each second member 36 and 38 has a length of from about 55 mm to about 58 mm, a width of from about 3 mm to about 6 mm and a thickness of from about 1 mm to about 3 mm, which thickness is preferably the same as that of elongated body 12.

Second elongated slot 42 has a proximal end 50 and a distal end 52 and defines an opening 78 having a length of from about 35 mm to about 40 mm and a width varying from about 8 mm at proximal end 50 to about 3 mm at distal end 52.

Similarly to first cursor 60, in an embodiment, second cursor 68 includes a rectangular surface element 70 attached to a round surface element (not shown) through a channel portion (not shown). As with first elongated slot 40 shown in FIGS. 1 and 2, upper surface 20 of body 12 contains markings 26 positioned along elongated slot 46 and bearing height units. Upper surface 20 is also marked with the word "height" at a location next to distal end 18 of body 12. Second cursor 68 is configured to slide along height markings 26 of second elongated slot 42. In an embodiment, the rectangular surface element 70 of second cursor 68 is from about 14 mm to about 18 mm in length and from about 10 mm to about 14 mm in width. Round surface element is configured to abut against the lower surface of the elongated member and is slidable along the second elongated slot. Round surface element of second cursor 68 has a circumference of from about 8 mm to about 10 mm. The channel portion can be from about 6 mm to about 8 mm in width and from about 1 mm to 3 mm in height.

Figure 2B:
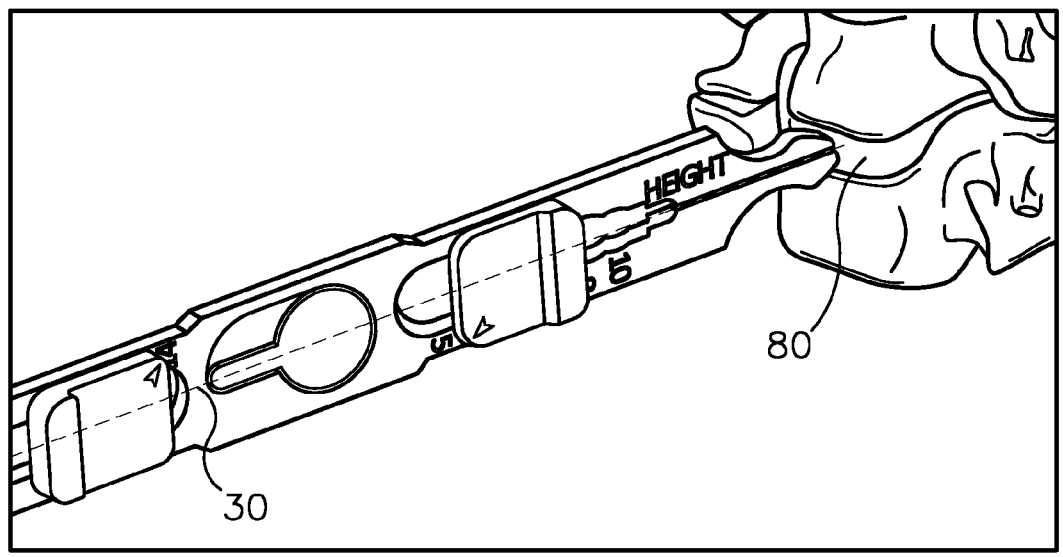
FIG. 2B is an illustration of the measuring device shown in FIG. 1 in operation to evaluate the height of an intradiscal space.

In use, as illustrated in FIG. 2B, it is envisioned that measuring device 10 is inserted into intradiscal space 80 at the distal end 18 of body 12 such that the longitudinal axis 30 is perpendicular to the plane of intradiscal space 80. The second cursor 68 can then slide along second elongated slot 42 urging second pair of members 38 and 40 apart until a correct height dimension of intradiscal space 80 is reached and the intradiscal height can be read.

With further reference to FIGS. 1 and 2, in an embodiment, central portion 16 of elongated body 12 includes a detachable stop 54. Detachable stop 54 has a round surface element 56 proximate and cooperatively attached to the second pair of members 36 and 38. Detachable stop 54 also has an elongated end portion 58 proximate and cooperatively attached to the first pair of members 32 and 34. In one aspect, round surface element 56 of detachable stop 54 has a diameter from about 10 mm to about 14 mm. Elongated portion 58 of detachable stop 54 has a length, in some embodiments, from about 25 mm to about 30 mm.

With further reference to FIGS. 1 and 2, the first pair of members 32 and 34 further define at least one opening 44 at proximal end 14 of body 12, the at least one opening configured to be aligned with depth markings 28 present on the lower surface 22 of body 12 at proximal end 14. In a preferred embodiment, the at least one opening 44 may be shaped as a square but other shapes that could accommodate detachable stop 54 are also contemplated. Measuring device 10 is also marked with the word "depth" on the lower surface 22 of body 12 at proximal end 14. The markings, in some embodiments, may comprise indicator markings (e.g., numbers, lines, letters, radiographic markers, color, etc.) disposed on portions or all of the device. Radiographic markers will permit the user to track movement, size, depth and/or width at the site over time using various diagnostic imaging procedures. Such diagnostic imaging procedures include, for example, X-ray imaging or fluoroscopy. Examples of such radiographic markers include, but are not limited to, barium, calcium phosphate, bismuth, iodine, tantalum, tungsten, and/or metal beads or particles.

Figure 3B:
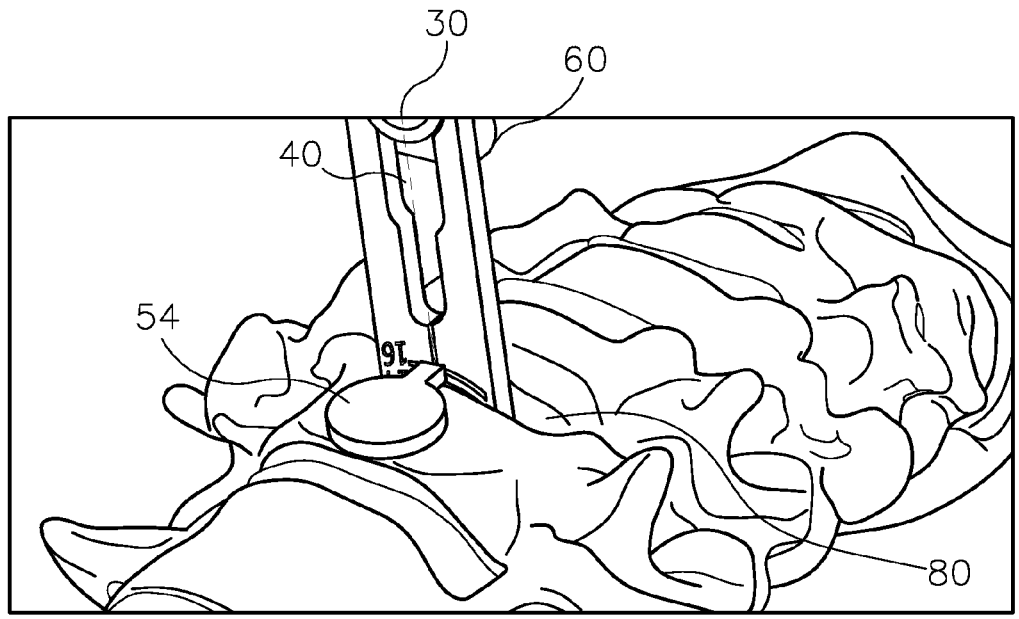
FIG. 3B is a perspective view of a spine section illustrating the measuring device shown in FIG. 3 in operation to evaluate the depth of an intradiscal space.
Figure 3C:
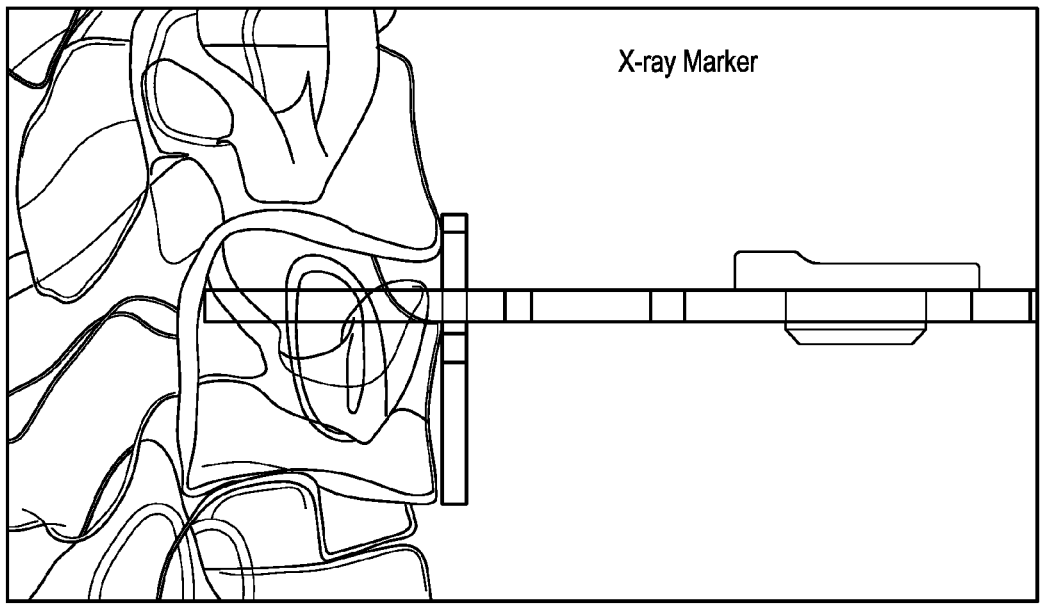
FIG. 3C is an illustration of an X-ray view of a spine section showing a portion of the measuring device in use to asses an intradiscal depth by C-arm fluoroscopy.

In use, as illustrated in FIGS. 3A and 3B, lower surface 22 of body 12 is inserted in intradiscal space 80 such that the longitudinal axis 30 is in the same plane as intradiscal space 80. Detachable stop 54 is removed from central portion 16 and inserted into the at least one opening 44 at the proximal end 14 of body 12 on lower surface 22 such that a correct depth measurement is obtained. In a preferred embodiment, detachable stop 54 and/or proximal end 14 of body 12 are provided with an x-ray marker allowing for the assessment of the intradiscal depth via C-arm fluoroscopy.

The components of the measuring device 10 described herein can be fabricated from biologically acceptable materials suitable for medical applications and/or their composites, depending on the particular application and/or preference of a medical practitioner. In some embodiments, the measuring device 10 or the components of device, individually or collectively, can be fabricated from materials such as polyaryletherketone (PAEK) including polyetheretherketone (PEEK), polyoxymethylene (POM), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, or combinations thereof.

Various components of the device may have material, including the above materials, to achieve various desired characteristics such as strength, rigidity, elasticity, compliance, and/or biomechanical performance. The components of the device, individually or collectively, may also be fabricated from a heterogeneous material such as a combination of two or more of the above-described materials. In some embodiments, the device or portions thereof may be made from radio-opaque materials. In some embodiments, the device or portions thereof may be made from radiolucent materials.

Although the measuring device 10 described herein is an intradiscal measuring device for selecting an optimal size cervical spacer allowing the assessment of the proper size implant with respect to width, height and depth for a patient undergoing a total disc removal or spinal fusion procedure, it is understood that the device 10 is not limited to use with this type of procedure and may be used in connection with a variety of other medical procedures, including, but not limited to, hip, knee and shoulder arthroplasty procedures or other areas of the spine (e.g., thoracic and/or lumbar).

It is envisioned that all or only a portion of the measuring device may have alternate surface configurations, such as, for example, rough, arcuate, undulating, porous, semi-porous, crescent, dimpled, polished and/or textured according to the requirements of a particular application. It is also contemplated that the measuring device may have alternate cross section configurations, such as, for example, oval, oblong, triangular, rectangular, square, polygonal, irregular, tubular, non-tubular, uniform, non-uniform, variable and/or tapered.

In some embodiments, the device may be lightweight, disposable and sterilizable. In some embodiments, one or more components of the device are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in some embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In some embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Other methods may also be used to sterilize one or more components of the device, including, but not limited to, gas sterilization, such as, for example, with ethylene oxide or steam sterilization.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A measuring device comprising an elongated body having an upper surface, a lower surface, a proximal end and a distal end, the elongated body including:
   a first pair of members configured for receiving a first cursor slidably arranged for measuring a width dimension;
   a second pair of members configured for receiving a second cursor slidably arranged for measuring a height dimension; and
   a detachable stop positioned in a central portion of the elongated body and operatively connected to the first pair of members and the second pair of members, the detachable stop insertable into at least one opening located at the proximal end of the elongated body, the detachable stop configured for measuring a depth dimension.

2. The measuring device of claim 1, wherein the elongated body is insertable into an intradiscal space.

3. The measuring device of claim 2, wherein the intradiscal space comprises a cervical, thoracic and/or lumbar vertebrae.

4. The measuring device of claim 1, wherein at the proximal end of the elongated body the upper surface further comprises markings for measuring the width dimension.

5. The measuring device of claim 1, wherein at the distal end of the elongated body the upper surface further comprises markings for measuring the height dimension.

6. The measuring device of claim 5, wherein at the proximal end of the elongated body the lower surface is provided with an X-ray marker for detection of the depth dimension by C-arm fluoroscopy.

7. The measuring device of claim 5, wherein the detachable stop is provided with an X-ray marker for detection of the depth dimension by C-arm fluoroscopy.

8. The measuring device of claim 1, wherein at the proximal end of the elongated body the lower surface further comprises markings for measuring the depth dimension.

9. The measuring device of claim 1, wherein the measuring device is made from a medical grade polymer selected from the group consisting of polyoxymethylene, polyether ether ketone or a combination thereof.

10. The measuring device of claim 1, wherein the measuring device is disposable.

11. The measuring device of claim 1, wherein the measuring device is deliverable in a disposable sterile package.

12. The measuring device of claim 1, wherein along a longitudinal axis of the elongated body the first pair of members defines a first elongated slot configured for receiving a first cursor, the first cursor slidable for urging apart the first pair of members until a width dimension is measured.

13. The measuring device of claim 1, wherein the second pair of members defines along a longitudinal axis of the elongated body a second elongated slot configured for receiving a second cursor, the second cursor slidable for urging apart the second pair of members until a height dimension is measured.

14. The measuring device of claim 1, wherein each of the first cursor and second cursor includes a plate portion cooperatively attached to a round surface portion, the round surface portion abutting against the lower surface of the elongated member and slidable along the first elongated slot or the second elongated slot.

15. A method of measuring the width, height and depth of an intradiscal space, comprising:
providing a measuring device according to claim 1;
inserting the first pair of arms into the intradiscal space such that the longitudinal axis of the elongated body is in the same plane as the intradiscal space and slidably adjusting the first cursor to read the width of the intradiscal space;
inserting the second pair of arms into the intradiscal space such that the longitudinal axis of the elongated body is perpendicular the plane of the intradiscal space and slidably adjusting the second cursor to read the height of the intradiscal space; and
inserting the detachable stop in the at least one opening at the proximal end on the lower surface of the elongated body such that the detachable stop is flush with a selected vertebra to read the depth dimension of the intradiscal space.

16. The method of claim 15, further comprising:
providing the proximal end or the detachable stop with an x-ray marker; and
reading the x-ray marker with C-arm fluoroscopy in order to assess the intradiscal depth.

17. The method of claim 15, further comprising:
providing the detachable stop with an x-ray marker; and
reading the x-ray marker with C-arm fluoroscopy in order to assess the intradiscal depth.

18. The method of claim 15, wherein the measuring device is disposable.

19. A measuring device comprising:
an elongated body extending along a central longitudinal axis, the elongated body having an upper surface, a lower surface, a proximal end and a distal end, the proximal end and the distal end operatively connected by a central portion containing a detachable stop, the elongated body further comprising:
a first pair of members extending from the central portion along the central longitudinal axis towards the proximal end of the elongated body, the first pair of members adjacent each other and defining a first elongated slot configured to receive a first cursor slidable to measure a width dimension, the first pair of members further defining at least one opening at the proximal end of the elongated body, the at least one opening configured for receiving the detachable stop insertable into the at least one opening to measure a depth dimension; and
a second pair of members extending from the central portion along the central longitudinal axis towards the distal end of the elongated body, the second pair of members adjacent each other and defining a second elongated slot configured to receive a second cursor slidable to measure a height dimension.

* * * * *